(12) United States Patent
Doctor et al.

(10) Patent No.: US 7,763,472 B2
(45) Date of Patent: Jul. 27, 2010

(54) METHODS FOR IDENTIFYING AND MEASURING S-NITROSOTHIOL BONDS IN HEME-CONTAINING CELLS AND MOLECULES

(75) Inventors: Allan Doctor, St. Louis, MO (US); Benjamin M. Gaston, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 890 days.

(21) Appl. No.: 11/630,010

(22) PCT Filed: Jun. 16, 2005

(86) PCT No.: PCT/US2005/021327

§ 371 (c)(1),
(2), (4) Date: Dec. 18, 2006

(87) PCT Pub. No.: WO2006/007403

PCT Pub. Date: Jan. 19, 2006

(65) Prior Publication Data

US 2007/0202605 A1    Aug. 30, 2007

Related U.S. Application Data (60) Provisional application No. 60/580,263, filed on Jun. 16, 2004, provisional application No. 60/631,506, filed on Nov. 29, 2004, provisional application No. 60/646,748, filed on Jan. 25, 2005.

(51) Int. Cl.
*G01N 33/52* (2006.01)
*G01N 33/50* (2006.01)
*G01N 33/68* (2006.01)

(52) U.S. Cl. .................. 436/107; 436/43; 436/52; 436/66; 436/86; 436/116; 436/120; 436/172; 436/177; 436/181

(58) Field of Classification Search .......... 436/43, 436/52, 107, 116, 172, 177, 181, 66, 86, 436/120
See application file for complete search history.

(56) References Cited

U.S. PATENT DOCUMENTS 5,891,735 A  4/1999  Stamler
2004/0203068 A1  10/2004  Mannick et al.

OTHER PUBLICATIONS

Dicks, A. P. et al, Journal of the Chemical Society, Perkin Transactions 2 1996, 481-487.*
Gow, A. J. et al, Journal of Biological Chemistry 1997, 272, 2841-2845.*
Ho, Y.-S. et al, Molecular Carcinogenesis 1999, 26, 201-211.*
Mannick, J. B. et al, Journal of Cell Biology 2001, 154, 1111-1116.*
Vanin, A. F. et al, Nirtic Oxide 2002, 7, 194-209.*

(Continued)

*Primary Examiner*—Arlen Soderquist
(74) *Attorney, Agent, or Firm*—Rodney L. Sparks (57) ABSTRACT

The invention provides a method of detecting an S-nitrosothiol in a sample which includes treating the sample with a transition metal such as copper (I) and cysteine in the presence of a substance capable of blocking interactions between iron-containing compounds and NO and detecting the generated NO.

22 Claims, 3 Drawing Sheets

OTHER PUBLICATIONS

Foster, M. W. et al, Trends in Molecular Medicine 2003, 9, 160-168.*

Allan Doctor, et al., "Hemoglobin conformation couples erythrocyte s-nitrosothiol content to O2 gradients," Proceedings of the National Academy of Sciences of the United States of America, The National Academy of Sciences of the USA, vol. 102 (No. 16), p. 5709-5714, (Apr. 19, 2005).

T. Govind Pai, et al., "Use of a chemiluminescence detector for quantitation of nitric oxide produced in assays of denitrifying enzymes," Analytical Biochemistry, Academic Press Inc., p. 150-157, (Mar. 6, 1987).

James F. Brien, et al., "Quantitation of nitric oxide formation from nitrovasodilator drugs by chemiluminescence analysis of headspace gas," Journal of Pharmacological Methods, Elsevier Science Publishing Co. Inc., p. 19-27.

D. Lyn H. Williams, "The chemistry of S-nitrosothiols," Accounts of Chemical Research, American Chemical Society, vol. 32 (No. 10), p. 869-876.

Kezhong Fang, et al., "Reductive Assays for S-nitrosothiols: Implications for measurements in biological systems," Biochemical and Biophysical Research Communications, Academic Press, p. 535-540.

David Jourd'Heuil, et al., "Effect of superoxide dimutase on the stability of S-nitrosothiols," Archives of Biochemistry and Biophysics, Academic Press, vol. 361 (No. 2), p. 323-330, (Jan. 15, 1999).

Ruth E. Bundy, et al., "A redox-based mechanism for nitric oxide-induced inhibition of DNA synthesis in human vascular smooth muscle cells," British Journal of Pharmacology, Macmillan Publishers Ltd., p. 1513-1521.

Jennifer D. Artz, et al., "In vitro activation of soluble guanylyl cyclase and nitric oxide release: A comparison of NO donors and NO mimetics," Biochemistry, American Chemical Society, p. 9256-9264.

* cited by examiner

METHODS FOR IDENTIFYING AND MEASURING S-NITROSOTHIOL BONDS IN HEME-CONTAINING CELLS AND MOLECULES

This application is a national stage filing of International Application No. PCT/US2005/021327, filed on Jun. 16, 2005, which is entitled to priority pursuant to 35 U.S.C. §119(e) to U.S. provisional patent application Nos. 60/580,263, filed Jun. 16, 2004, 60/631,506, filed Nov. 29, 2004, and 60/646,748, filed Jan. 25, 2005 the entire disclosures of which are hereby incorporated by reference herein.

STATEMENT REGARDING FEDERALLY SPONSORED RESEARCH AND DEVELOPMENT

This invention was made in part using funds obtained from the United States Government under Grant Nos. R01 HL 59337 and K08 GM069977, awarded by the National Institutes of Health. The United States Government may have certain rights in the invention.

BACKGROUND

S-Nitrosothiols (SNOs) signal a variety of biological activities in cells and tissues. Studies of SNO signaling are hampered by a lack of reliable assays. This has been particularly true for assays of SNO bonds and iron/porphyrin-containing cells and proteins, where autocapture of nitric oxide (NO) by iron after cleavage of the SNO bond alters/attenuates the assay signal. Though there is general agreement, for example, that a SNO bond is formed at the $\beta^{93}$ cysteine of hemoglobin under physiological conditions, results vary substantially depending on assay technique. Moreover, efforts to protect against 1) artifactually measuring FeNO bonds (by photolysis); 2) artifactually forming FeNO or SNO bonds; and 3) artifactually dampening the signal by autocapture on the iron group, have led to complex assays requiring extensive hemoglobin pretreatment (with cyanide, N-ethyl-maleamide and a variety of other reagents) before the SNO bond can be assayed. These extreme chemical conditions have given rise to substantial controversy about issues such as whether SNO bond stability is affected by hemoglobin allostery. Moreover, the most reliable assays for SNO and FeNO bonds in hemoglobin and in other protein S-nitrosothiols require expensive and cumbersome equipment.

It has recently become evident that SNO signaling is deranged in a variety of human diseases, ranging from asthma to cystic fibrosis. SNO hemoglobin related signaling appears to be abnormal in sepsis, diabetes, pulmonary hypertension, and sickle cell anemia and congestive heart failure. Reliable SNO protein assays are likely to be relevant not only to in vitro cell culture work and physiology experiments, but also to clinical assays, particularly human clinical assays. Increased SNO loading and improved allosteric delivery of NO can improve perfusion to a variety of organs. On the other hand, when SNO loading is excessive, normal vasoregulation—particularly in the lung—can be blunted. Assays for NO hemoglobin may be of critical importance to improving health care over the next several decades, and it has been known for over a decade that NO circulates in the plasma of healthy humans.

A wide spectrum of analytical approaches and sample manipulation in recent years have yielded highly divergent values of S-nitrosothiol content in plasma or other fluids or tissues, often within a range of three orders of magnitude (see Giustarini et al., Clinica Chimica Acta, 2003, 330:85-98, for a review). For example, the various techniques and assays have found nitrosothiol levels ranging from 15 to 7,000 mmol/l, in serum or plasma.

S-nitrosothiols in biological samples have been measured by a wide spectrum of different techniques, e.g., chemiluminescence, calorimetric, amperometric, spectrophotometry, HPLC, GC-MS and fluorescence-based methods (Cook et al., Analytical Biochemistry, 1996, 238:150-158, Fang et al., Biochemical and Biophysical Research Communications, 1998, 252:535-540, Giustarini et al., Clinica Chimica Acta, 2003, 330:85-98, Jourd'Heuil et al., Free Radical Biology & Medicine, 2000, 28:3:409-417, Palmerini et al., Biology and Chemistry, 1998, 2:5:375-380, Palmerini et al., Biology and Chemistry, 1998, 2:5:375-380, Palmerini et al., Biology and Chemistry, 2000, 4:6:546-549, Park et al., Analytical Biochemistry, 1997, 249:61-66, Pfeiffer et al., Analytical Biochemistry, 1998, 258:68-73, Samouilov et al., Analytical Biochemistry, 1998, 258:322-330, Stubauer et al., Journal of Biological Chemistry, 1999, 274:40:28128-28133, and Tsikas et al., Journal of Chromatography, 2002, 772:335-346.). However, these techniques are not devoid of artifacts and the investigation of endogenous S-nitrosothiol levels is therefore hampered by methodological concerns.

For example, the spectrophotometric assay involves the colorimetric measurement of $NO_2^-$ after displacement by $HgCl_2$ by reaction with Griess solution. This technique is very simple, but has a relatively high detection limit (0.5 µmol/l). In addition, it has been suggested that mercury does not stoichiometrically release NO from RSNOs when added to plasma Assuming that plasma or tissue S-nitrosoprotein levels are very low, artifactual overestimation is a problem. Therefore, sample manipulation also assumes a critical role. The relative instability of RSNOs in some conditions has been demonstrated, in particular, in the presence of metals that can induce their decomposition. Moreover, it is known that the artifactual formation of S-nitrosothiols from nitrite and SH groups under acidic conditions occurs. In addition, the evaluation of RSNOs can be influenced by the occurrence of transnitrosation reactions interchanging the $NO^+$ moiety between two sulfhydryl groups. S-nitrosothiol assays must also take into account the high background concentration of nitrites present in biological samples, which can be responsible for some overestimated determinations. This anion can be removed by reaction with ammonium sulfamate via their reduction to nitrogen gas.

There is a long felt need in the art for a reliable and accurate method of detecting or measuring S-nitrosothiols in the broad range of samples researchers and medical practitioners encounter without need to change the method for different types of samples. The present invention satisfies this need.

SUMMARY OF THE INVENTION

The present invention is directed toward a method of detecting and/or measuring S-nitrosothiols. The method comprises reacting a test sample with cysteine, Cu(I) ions, and an iron blocking agent in an anaerobic aqueous solution and then detecting the evolved gas phase NO. The detection system for NO can be any analyzer suitable for detecting NO, though it is ideally embodied by a chemiluminescence device or other device sensitive to low pmole quantities of NO.

The method is applicable to a range of test samples including, but not limited to, blood, sweat, tears, urine, feces, plasma, amniotic fluid, airway lining fluid/bronchoalveolar lavages, cerebrospinal fluid, joint fluid, pleural fluid, peritoneal fluid, cervical fluid, semen, tissue, cells, synthesized compounds, and derivatives, fractions, extracts, and isolates thereof. In one aspect, the cells are red blood cells. The samples can be from an animal, more preferably, a mammal, or even more preferably, a human.

When cells are used, they can be added intact, i.e., as whole cells, or they can be lysed by any appropriate method prior to reaction, or they can be lysed in the process of being analyzed, or they can be processed by any combination of these methods. Such lysis methods are applicable during both pre-analysis and analysis of the sample. Lysis techniques include, but are not limited to, addition of a lysing agent such as an enzyme, a detergent, a surfactant, exposure to hypotonic or hypertonic conditions, pressure gradient, ultrasonic treatment, freezing, thawing, irradiation, turbulence, treatment with chemicals, and treatment with solvents.

A further embodiment of the invention can include the use of a purge gas to direct the generated NO to the NO analyzer. This purge gas can comprise an inert gas. For the purposes of this invention, an inert gas is simply a gas that does not participate in a reaction with S-nitrosothiols or NO under the conditions where these compounds are present in this method. Suitable inert gases include, but are not limited to, nitrogen, helium, argon, krypton, and xenon, as well as yet undiscovered inert gases which have suitable properties to be used in place of helium in the method of the invention. This inert gas may optionally be a highly purified gas, for example grade 5 helium, and may also optionally be helium or another gas that has been treated to remove residual carbonyls that were introduced during purification of the gas or came to be present in the gas in some other way. The method for removing the carbonyls would be by any method known to those skilled in the art and includes, but is not limited to, removal with iodine crystals and activated carbon granules.

A further embodiment of the invention comprises the addition of compounds that will bind to iron, to iron porphyrin, or to hemoglobin so as to prevent these chemical entities from interfering with the analysis by binding the NO generated and preventing its subsequent detection. Suitable compounds include, but are not limited to carbon monoxide (CO) gas, blended with the carrier gas.

A further embodiment of the invention includes techniques for accounting for interferences from carbonyls or other contaminants that may be present in the CO gas or carrier gas, or noise by running a blank before, after, or separately from the test sample or by adjusting a baseline response of the analyzer prior to testing a sample.

A further embodiment of the invention comprises its use in the presence of compounds and/or cells containing hemporphyrin groups. The presence of these hemeporphyrin groups may be due to, but is not limited to, the presence of red blood cells or hemoglobin.

A further embodiment of the invention comprises its use to distinguish S-nitrosothiols from nitrite, nitrate and peroxynitrite. The system of reduction in Cu (I) and cysteine, when carried out at neutral pH, does not form NO in the presence of nitrite, nitrate or peroxynitrite, but only in the presence of S-nitrosothiols. Therefore, the system selectively detects S-nitrosothiols among a mixture of other NO-related compounds.

Further embodiments of the present invention comprise the use of cysteine concentrations from about 0.1 mM to about 10.0 mM, copper (I) concentrations from about 0.1 μM to about 10.0 μM, reaction temperatures from about 40° C. to about 80° C., reaction pressures from about 0 to about 1,500 Torr, and reaction pH from about 5.0 to about 8.0.

The present application discloses an invention which is an improvement over previous methods, wherein said new method measures SNO proteins, even in the presence of a vast excess of heme porphyrin groups. This technology is likely to have broad application in the biomedical industry.

It will be appreciated that, although the present invention is discussed in terms of what is perhaps its most useful application, the measurement of S-nitrosothiols in a particular type of sample, it may be employed to detect and measure S-nitrosothiols of any sample no matter how obtained, no matter the source, and no matter how treated.

The foregoing and other features, objects, and advantages of the present invention will be apparent from the following detailed description, the scope of the invention being set forth in the appended claims.

BRIEF DESCRIPTION OF THE DRAWINGS

FIG. 1 schematically depicts steps and devices of the assay system of the invention. A copper cysteine solution is saturated with CO by continuous passage of a gas stream through the reaction solution. S-nitrosothiol bonds are reduced to NO by reaction in the copper cysteine solution. Retention of NO by any Fe present is prevented by preferential interaction of Fe with CO. NO, selective produced by reduction of S-nitrosothiol bonds in a sample, is then free to be carried by the gas stream to the nitric oxide analyzer for quantification.

DETAILED DESCRIPTION OF THE INVENTION

Definitions and Abbreviations

3C—carbon monoxide-saturated copper-cysteine
CO—carbon monoxide
CN—cyanide
Cu—copper
Cys—cysteine
DEA/NO—diethylamine NONOate
Fe—iron
Hb—hemoglobin
He—helium
Hg—mercury
GSNO—S-nitrosoglutathione
RBC—red blood cell
RT—room temperature
SNO—S-nitrosothiol(s)

SNP—sodium nitroprusside
SNAP—S-nitroso-N-acetylpenicillamine
SIN-1—3-morpholinosydnonimine
Sper/NO—spermine NONOate For purposes of the description of this invention, the articles "a" and "an" are used herein to refer to one or to more than one (i.e. to at least one) of the grammatical object of the article. By way of example, "an element" means one element or more than one element.

The term "aberrant S-nitrosothiol levels or aberrant S-nitrosothiol signaling," as used herein, refers to S-nitrosothiol levels or S-nitrosothiol signaling which are higher or lower S-nitrosothiol levels or S-nitrosothiol signaling than normally found in a subject.

As used herein, "anaerobic conditions" means that no oxygen is present.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined for the presence and/or quantity of SNO.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, but are not limited to, radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

As used herein, a "peptide" encompasses a sequence of 2 or more amino acid residues wherein the amino acids are naturally occurring or synthetic (non-naturally occurring) amino acids covalently linked by peptide bonds. No limitation is placed on the number of amino acid residues which can comprise a protein's or peptide's sequence. As used herein, the terms "peptide," polypeptide," and "protein" are used interchangeably. Peptide mimetics include peptides having one or more of the following modifications:

1. peptides wherein one or more of the peptidyl —C(O)NR— linkages (bonds) have been replaced by a non-peptidyl linkage such as a —CH$_2$-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) wherein R is $C_1$-$C_4$ alkyl;
2. peptides wherein the N-terminus is derivatized to a —NRR$_1$ group, to a —NRC(O)R group, to a —NRC(O)OR group, to a —NRS(O)$_2$R group, to a —NHC(O)NHR group where R and R$_1$ are hydrogen or $C_1$-$C_4$ alkyl with the proviso that R and R$_1$ are not both hydrogen;
3. peptides wherein the C terminus is derivatized to —C(O)R$_2$ where R$_2$ is selected from the group consisting of $C_1$-$C_4$ alkoxy, and —NR$_3$R$_4$ where R$_3$ and R$_4$ are independently selected from the group consisting of hydrogen and $C_1$-$C_4$ alkyl.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and Xaa or X is any amino acid. Other naturally occurring amino acids include, by way of example, 4-hydroxyproline, 5-hydroxylysine, and the like.

Synthetic or non-naturally occurring amino acids refer to amino acids which do not naturally occur in vivo but which, nevertheless, can be incorporated into the peptide structures described herein. The resulting "synthetic peptide" contains amino acids other than the 20 naturally occurring, genetically encoded amino acids at one, two, or more positions of the peptides. For instance, naphthylalanine can be substituted for tryptophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;

III. Polar, positively charged residues:
His, Arg, Lys;
IV. Large, aliphatic, nonpolar residues:
Met Leu, Ile, Val, Cys
V. Large, aromatic residues:
Phe, Tyr, Trp As used herein, the term "purge vessel" refers to the glassware or chamber in which the reaction occurs. The term "purge vessel" is used interchangeably herein with the terms assay, reflux, and reaction chamber or vessel.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

The term "standard," as used herein, refers to something used for comparison. For example, it can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured. The term "standard sample" refers to a sample comprising a known amount of NO, or a series of samples comprising varied known amounts of NO, which is used for comparison or is used to generate a standard curve of values for comparison to a test sample which is being subjected to analysis of NO generated from nitrosothiol.

A "subject" of analysis, diagnosis, or treatment is an animal. Such animals include mammals, preferably a human.

A "transition metal," as used herein, refers to an element which forms at least one ion with partially filled d shell of electrons. A "transition metal," as used herein, also refers to any element in the d-block of the periodic table, including zinc and cadmium. This corresponds to periodic table groups 3 to 12 inclusive.

Figure 1:
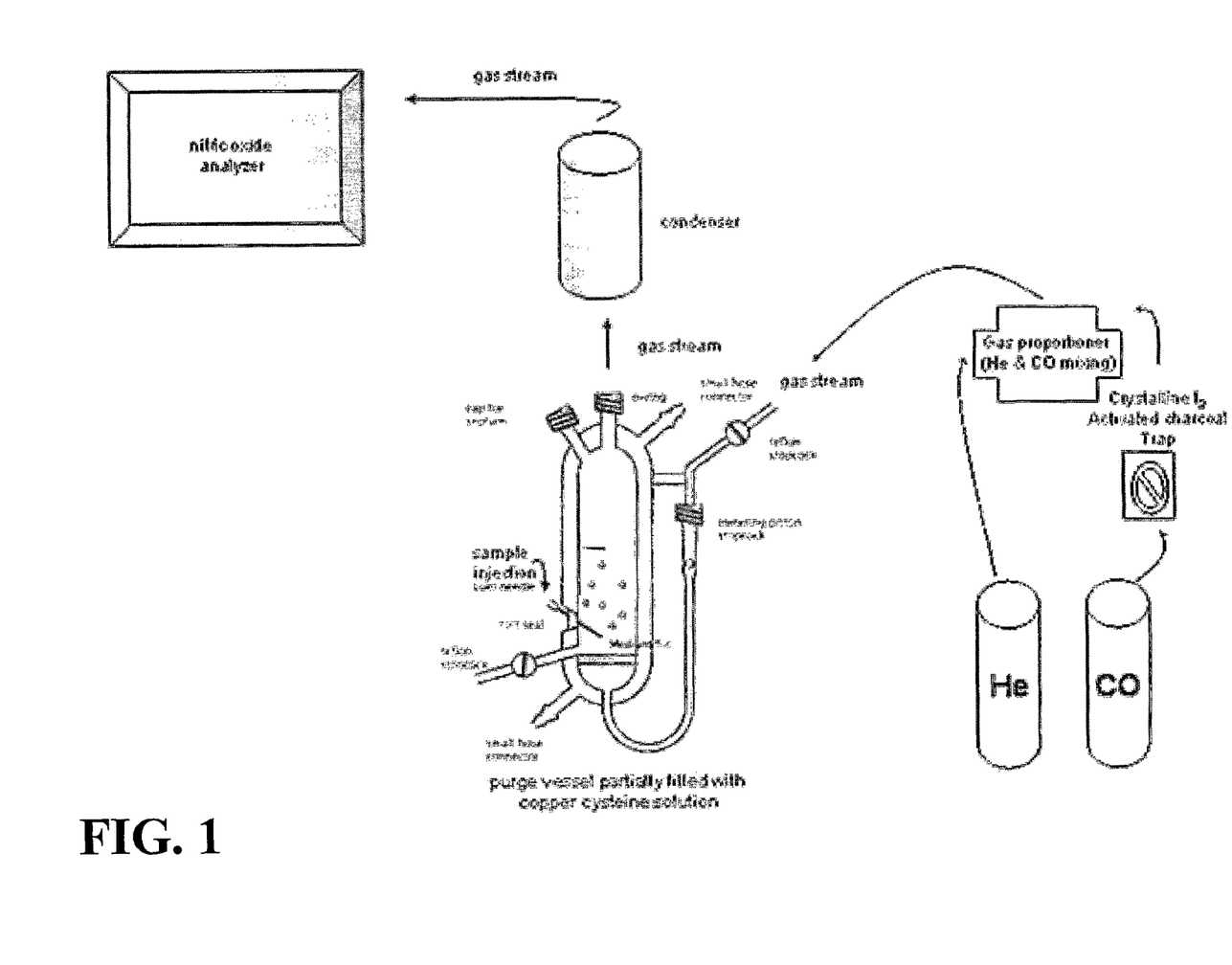

The present invention presents a method of detecting and/or measuring the S-nitrosothiol content of a sample. This method can be used on biological samples or on synthesized compounds. One embodiment of the invention is illustrated in FIG. 1.

In one embodiment, purification of the sample prior to this analysis may be done. Examples of biological samples that the present method is applicable to include whole cells, lysed cells, cell extracts, cell isolates, biological fluids, biological waste products whether liquid or solid, and combinations of these. These biological samples may be obtained from animals generally, or more preferably, from mammals, or even more preferably, from humans. Additionally, the sample may be produced in vivo, as in the case of a sample of blood taken from a human or other mammal, or in vitro as in the case of cell cultures, treated biological materials or synthesized compounds. These example sources of samples should not be viewed as limiting the scope of the invention, as they are merely illustrative of a few possible sources of the sample to be analyzed. The invention itself is related to the method of analysis of a sample wherever or however obtained.

Intact cells, when present alone or with other sample materials, can be lysed. Such lysis can be performed separate from, prior to, or during the analysis and may be performed by any appropriate means. Examples of some possible methods of lysis include ultrasonic treatment, application of pressure gradients, high shear, addition of one or more lysing agent, osmotic methods (e.g. exposure to hypotonic conditions), heating, freezing, and freeze-thaw cycling. These examples should not be viewed as limiting, but merely as examples of some techniques that can be used to lyse the cells. Lysing agents include, but are not limited to, enzymes, solvents, alcohols, detergents, acetone, salts, and surfactants. An additional embodiment of the invention includes dilution of the sample sufficient such that heme proteins become dimers and lose allosteric regulation (<100 µM); and one in which cells are left intact, and not lysed, and/or the sample is not diluted.

S-Nitrosothiol compounds are readily recognized by those skilled in the art as comprising a sulfur atom bound to a nitrogen atom which is bound to an oxygen atom. The present invention applies to detection or analysis of all such S-nitrosothiol compounds.

The particular method which is the subject of the present invention comprises reacting the sample with a combination of cysteine, copper (I) ions, and a reagent capable of preventing side reactions which prevent the generation of the NO or the absorption/adsorption of NO and gas analysis to detect or measure the NO generated.

The form of cysteine believed to participate in the reaction is the form commonly known as "reduced cysteine" which is contrasted to the oxidized form also referred to as "cystine." However, interconversion between these two forms is readily achieved by those skilled in the art through methods such as, but not limited to, addition of oxidation or reducing compounds. The invention is described herein as using "cysteine," but should also be understood to include cysteine that was generated before or during the reaction with the sample through conversion of cystine to cysteine. Similarly, copper (I) ions can be produced from metallic copper or from other valent forms of copper ions. This invention should be read as including such means of providing the copper (I) ions.

The additional reagent that prevents side reactions with, or absorption or adsorption of, NO includes compounds that prevent the combination of NO with iron or iron-containing molecules, cells, or substances. For example, CO can be added during the reaction as a means of preventing such binding of NO. Other compounds with similar properties to CO could also be added instead of CO, including compounds such as cyanide gas. As described herein, however, cyanide cannot be used in pretreatment of the sample. The reaction mixture may also comprise an ingredient or method that serves to prevent, limit, control, or eliminate foaming. Such foam control methods are readily known to those skilled in the art and include, but are not limited to addition of commercial antifoams, surfactants, silicone products, alcohols, fatty acids, polar organic compounds, detergents, and oils, as well as methods such as temperature control, temperature change, pressure control, pressure change, application of sonic energy, heated surfaces, application of shear, and application of light. However, these anti-foaming measures must not artifactually form NO or another compound that would be identified by the NO detector as NO.

The analysis for NO can be performed by any appropriate method for measuring or detecting NO. One such device, although not the only possible embodiment, is a device based on chemiluminescence, such as an NOA 280i (Sievers, Boulder Colo.) (See FIG. 1). This particular method of analysis measures the amount of light emitted during the reaction of NO and ozone. The NO generated in the method of the current invention can be introduced to the analyzer by any suitable means. Some applicable methods include but are not limited to techniques such as head space analysis, analysis of a purge stream, or analysis within the space of the reaction vessel itself.

A "purge stream" as used to describe this invention is intended to encompass all meanings as used by those skilled in the art. These meanings include, but are not limited to, "continuous," where a gas stream is continuously added to and emitted from the purge reaction vessel during the entire course of the analysis, "initially," where the gas is added to the chamber before the reaction or only at the beginning of the reaction and emitted at that time or later, "finally," where the introduction of gas begins anytime after the commencement of the reaction and is intended to indicate all situations not addressed by the use of the term "initially," and "intermittently," where the gas flow into or out of the reaction is started and stopped at intervals, said intervals being of uniform or varying times. The addition of gas to the vessel and the release of the gas may be simultaneous or sequential. Such purging may also comprise use of or application of vacuum to the reaction vessel.

Additionally, these methods of purging can be combined with each other and with other means not specifically described herein. The rate of gas flow may be measured or not measured and when measured it may be measured in its entirety or only a portion may be measured. Such gas flow measurement may be made of the gas entering the vessel or the gas exiting the chamber, or both. The analysis performed for the NO may be on the headspace, the entire exit stream or a portion of the exit stream, or on whatever other portion or location of the gas as allows the NO generated to be detected or measured. The invention also includes measurement of the NO gas once generated as absorbed, adsorbed into, or onto any suitable material by whatever other detection or measurement technique as may be suitable.

Measurement may be continuous or intermittent. Analysis of a gas stream may optionally include any appropriate pretreatment of the gas stream as may be desirable. Common pretreatments include, but are not limited to, separation of liquid carryover, condensation of water vapor, removal of particular molecular species, adjustment of temperature, or addition of a gas.

Test samples can be obtained from animals, including, but not limited to, mammals and humans, or alternatively from cultured cells or tissues. Samples obtained from such subjects include, but are not limited to, blood, sweat, tears, urine, feces, plasma, amniotic fluid, airway lining fluid/bronchoalveolar lavages, cerebrospinal fluid, joint fluid, pleural fluid, peritoneal fluid, cervical fluid, semen, tissue, cells, and derivatives, fractions, extracts, and isolates thereof Test samples, as well as control samples, can also be obtained by chemical synthesis.

Figure 3:
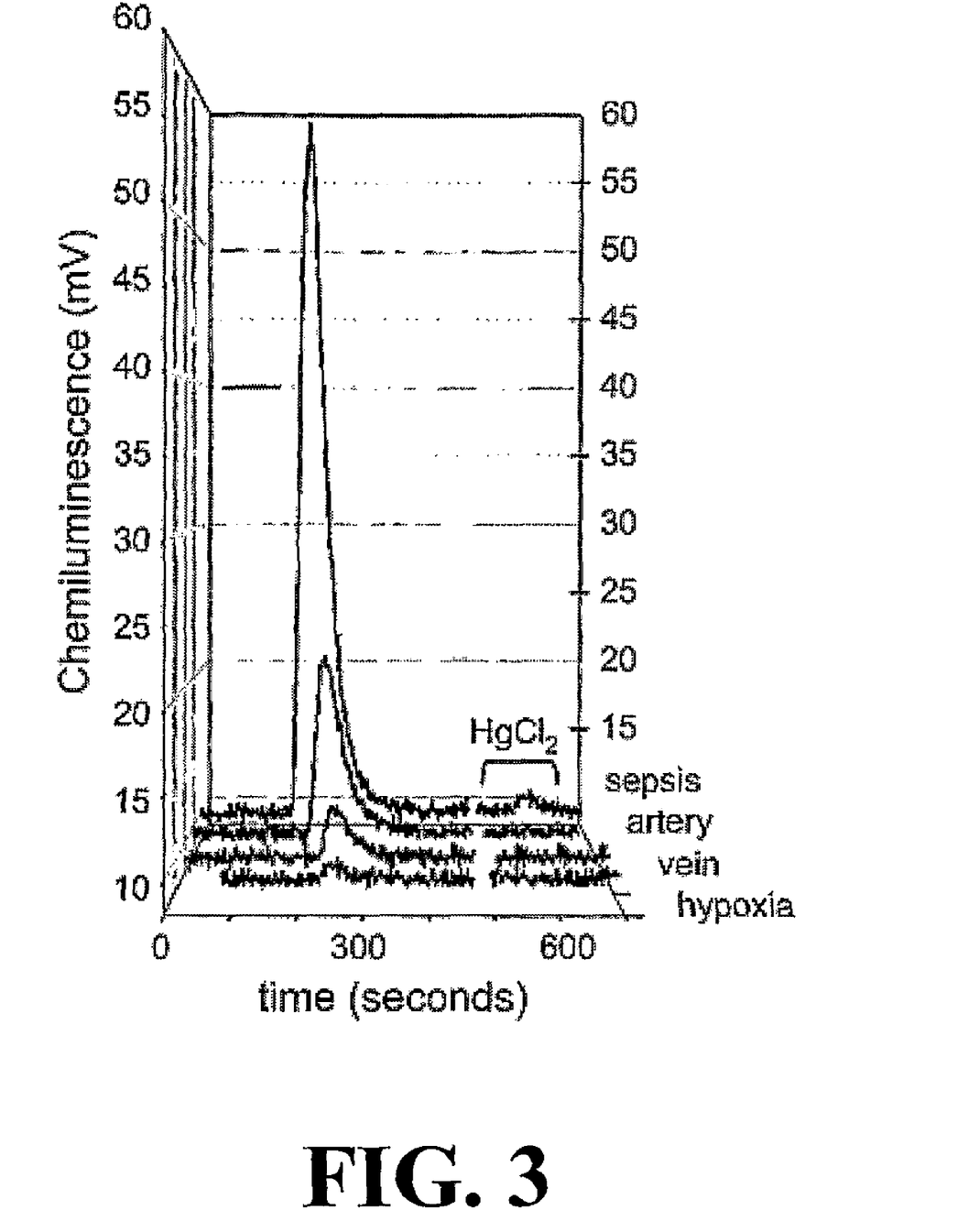
FIG. 3 graphically depicts raw chemiluminescence signals from intact human red blood cells (1 mM Hb±HgCl$_2$) under various conditions (sepsis; artery; vein; and hypoxia). Baselines are normalized for comparison. Specific data ranges for red blood cell S-nitrosothiol content ($SNO_{RBC}$) are provided in Table 1. The ordinate represents chemiluminescence in mV and the abscissa represents time in seconds.

In one embodiment, the Cu/cysteine/CO assay measures S-nitrosothiols in Hb isolated from erythrocytes. In another embodiment, instead of isolating Hb from erythrocytes, intact erythrocytes are injected into the assay chamber after washing in physiological buffer at the precise pH and $pCO_2$ at which the circulating erythrocytes had been drawn from the artery, vein, or capillary (See Table 1 and FIG. 3). The SNO-Hb concentration is derived from the evolved NO signal using the SNO-Hb in Hb and/or GSNO in Hb standard curve.

In another embodiment, whole blood is injected into the assay chamber instead of isolated RBC's or hemoglobin. The advantage is that no preparation is required at all except for (chelator-free) anticoagulation. A potential disadvantage is that SNO-proteins other than those in RBC's are identified, decreasing specificity. For example, this assay would identify SNO-albumin, despite the presence of Hb. Nevertheless, it may be of critical relevance to know the entire circulating SNO-content in a variety of disease states, including sepsis. In one aspect, an aliquot of the sample of blood can be subjected to another assay done in tandem with the SNO assay for other properties of blood relevant to hemoglobin allostery, including, but not limited to, partial pressure of oxygen and carbon dioxide, so that the results may be interpreted in tandem on an individual sample from a single time-point. In one aspect, the assay is performed on a subject undergoing therapy with a nitrovasodilator, including, but not limited, to, nitroprusside, nitroglycerine, inhaled NO or ethyl nitrite, for the purpose of monitoring efficacy and/or toxicity of the therapy. In one aspect, the sample is a red blood cell.

In one embodiment, the methods of the invention are used in tandem with conventional high-throughput assays for other allosterically regulated and non-allosterically regulated species in blood and/or hemoglobin. In one aspect, SNO-RBC content can be measured after conventional automated measurement of blood pH, pCO2, pO2, bicarbonate, and other species. This tandem automation can be applied to routine clinical laboratory measurement to guide clinical management of gas exchange, hemodynamic management, therapeutic titration and other issues.

The methods of the present invention also apply to biological fluids other than blood which may contain metalloproteins capable of dampening the NO signal in the carrier gas. Examples include, but are limited to, measuring SNO proteins in amniotic fluid, airway lining fluid/bronchoalveolar ravages, urine, cerebrospinal fluid, joint fluid, pleural fluid, peritoneal fluid, stool, cervical fluid and semen.

In one aspect, the methods of the invention can be applied to measuring the SNO content of tissues other than those in which there are other metalloproteins capable of dampening the NO signal in the carrier gas. For example, myocardial and other muscle biopsies can be assayed for SNO-proteins without interference from myoglobin.

In another aspect, the methods of the invention can be used to measure SNO content of cells in culture, or organelles, such as mitochondria, isolated from cell cultures in vitro, that contain metalloproteins.

In one aspect, the protein is cytochrome c.

In one embodiment of the invention, the method can be modified to accommodate a sample in which the SNO concentration is extremely low, by increasing the volume of the reflux chamber to allow injection of a larger sample.

The cell sample may also comprise cell byproducts, or cell derivatives. The form of the sample may be as a tissue sample, a fluid sample, a waste sample, as well as combinations of these and derivates of these. Such derivatives, both of cells and in reference to the sample form, can include, but are not limited to, lysates, extracts, isolates, products of reactions, separation fractions, dried, diluted, chemically treated, physically treated as well as combinations of these.

Without wishing to be bound by any particular theory, the method of the current invention is believed to involve the reaction of the S—NO bond with cysteine, (resulting in transnitrosation to form S-nitrosylated cysteine, CSNO), copper (I) ions (which catalyze the conversion of CSNO to oxidized cystine and NO gas), and carbon monoxide with metal groups in proteins that would otherwise interfere with the NO assay, classically including, but not being limited to, $Fe^{2+}$ porphyrin, in a solution that rapidly lyses the cells (due to hypotonic conditions or otherwise). Of course, if the sample does not consist of intact cells, conditions facilitating cell lysis are not necessary.

This reaction between the S-nitrosothiol and cysteine in the presence of copper (I) can take place within a range of different pHs and temperatures and within a range of concentrations of the reagents. One embodiment of the invention utilizes a temperature of about 40° C. to about 80° C. and a pH of about 5.0 to about 8.0. Another embodiment utilizes a pH of about 6.0 to about 7.0 and a temperature of about 50° C. to about 65° C. In general, at lower pH values and higher temperatures, the assay loses its specificity for S-nitrosothiols and can also detect nitrite. Therefore, a pH of greater than about 6.5 and a temperature of less than about 60° C. are generally preferred, because of the ubiquitous nature of nitrite.

In one aspect, a transition metal other than copper is used. In yet another aspect, the transitional metal is a non-iron transition metal. Transition metals include the elements Sc, Ti, V, Cr, Mn, Fe, Co, Ni, Cu, Zn, Y, Zr, Nv, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, and Uub.

When there is the possibility for interference from nitrite in the sample, pH can be adjusted to minimize the potential for conversion of this nitrite to NO and interfere with the analysis. However, the current method can still be utilized even at this low pH when there is no contaminating nitrite present or by removal of the nitrite or separate analysis of the nitrite. One such method, although not the only method and those skilled in the art can describe other means, would be to expose the sample to the low pH conditions in the reaction vessel, but without all of the reagents present. Such method can be used to remove and optionally measure the nitrite present. Another alternative is to measure content through a separate analytical means.

The reagent compositions can also be varied.

Sources of copper (I) are commonly known by those of ordinary skill in the art and include, but are not limited to, CuCl, CuI or CuBr. One of ordinary skill in the art would appreciate that copper (I) could be substituted with other transition metals in the practice of the present invention.

In the methods of the present invention, one or more enhancers of NO can be used. Enhancers of NO include, for example, NOS enhancers, and NO donors such as sodium nitroprusside (SNP), S-nitroso-N-acetylpenicillamine (SNAP), S-nitrosoglutathione (SNOG, GSNO), diethylamine NONOate (DEA/NO), DETA/NO (NOC-18), 3-morpholinosydnonimine (SIN-1) and spennine NONOate (Sper/NO).

In the methods of the present invention, at least one inhibitor of NO (e.g., NOS inhibitors) can be used. When more than one inhibitor is used in the methods of the present invention, the inhibitors can be the same or different. In a particular embodiment, two inhibitors of NO, such as two inhibitors of NOS (e.g., L-NAME and ETU), are used in the methods of the present invention.

In one embodiment, the methods of the invention are useful in measuring S-nitrosothiols in diseases, conditions, and disorders where S-nitrosothiol signaling or S-nitrosothiol levels are aberrant. Such diseases and disorders include, but are not limited to, asthma, cystic fibrosis, sepsis, diabetes, pulmonary hypertension, sickle cell anemia, inflammation, abnormalities of vasoregulation, and congestive heart failure.

Other methods useful for identifying, measuring, and quantifying protein nitrosylation and S-nitrosothiols are known to those of ordinary skill in the art and are available for use in the methods of the present invention. Publications describing such techniques are hereby incorporated in their entirety herein (see for example, U.S. Pat. No. 6,806,057 and U.S. Pat. Pub. Nos. 2004/0067595 and 2005/0026227, all of which are incorporated by reference in their entirety herein).

EXAMPLES

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out some embodiments of the present invention, and are not to be construed as limiting in any way the remainder of the disclosure. Therefore, the examples should be construed to encompass any and all variations which become evident as a result of the teaching provided herein.

Example 1

Assay for SNO-Hemoglobin Ex Vivo

Methods
Protocol: Copper Cysteine Assay for S-Nitrosothiols
1. Prepare fresh copper cysteine (Cu/cys) solution comprising 1 µM CuCl, 1 mM cysteine (4.9 mg copper (1+) chloride (Sigma #C3294, stored at room temperature ("RT"), bring to 500 ml with distilled $H_2O$, add 60.5 mg cysteine (Sigma #C7755, stored at −20° C. or 87.6 mg Sigma #C6852); adjust pH to 6.6 with 0.1N NaOH; store at room temperature; the solution should be prepared fresh daily).
2. Adjust water bath to 50° C. and cold water flow to the condenser.
3. Wash purge vessel with acetic acid, then with $H_2O$, finally with the Cu/cys solution.
4. Fill the reaction chamber with 3-5 ml of Cu/cys solution and adjust system. Data not shown demonstrate that a larger reflux chamber holding 10-15 mL of Cu cysteine and accommodating up to 1 mL of sample injection improves the ratio of signal-to-noise in the NO readout.
 a. Close lid to chamber.
 b. Close stopcock from He incoming line.
 c. Check for slight bubbling of Cu/cys by pump vacuum only.
 d. Re-open He stopcock and adjust the CO/He flow rate to give vigorous bubbling. The proportional amount of CO within the gas stream may be varied from 50-100% depending upon the molar quantity of transition metal within the purge vessel. Note that metal carbonyls (commonly at levels of 0.7 parts per million in research grade CO) must be removed, as both Ni- and Fe-carbonyls chemiluminesence in the presence of $O_3$. Therefore, the CO source gas must be passed through iodine crystals and (in series) activated charcoal and then blended with the He stream in a gas proportioner (Aalborg, Orangeburg, N.Y.). Of note: 1) oxidized cysteine should be replaced and residual Hb removed by refreshing the reflux chamber with 3C solution at frequent intervals; and 2) NP-40 and Triton X 100 both produce artifactual signal with this assay.
 e. Check the cell pressure (want ~7-10 torr), the supply pressure (want 5.5-6.5 psig), and the cooler temperature (want ~−10° C.), cell pressure with top-of-reaction chamber-stopcock shut off should be 3-5 torr (if not there is a leak in the line between the reaction chamber and the NOA cell), purge vessel pressure (typically ~700 Torr, but may be varied between 0 and 1,500 Torr) by adjusting the gas stream flow rate into the purge vessel.

f. Check the baseline chemiluminescence signal mV (want ~5-15 mV).

g. Add 100 μl antifoam solution (diluted 1->30 with deionized/distilled $H_2O$).

5. Prepare standard curve of GSNO (see following procedure), 20 μl/injection.

a. pre-inject SNO-depleted Hb prior to GSNO injection at Hb concentration and volume of unknown samples. Inject increasing concentrations of GSNO in the presence of Hb. Repeat the assay in the absence of Hb to ensure that CO is binding all the Hb iron—i.e., that there is no autocapture of GSNO-derived NO in Hb. The GSNO standard curves with and without Hb should be the same. Be sure to perform dilute enough standards that the curve is in the physiological range desired for measurement. Specificity of instrument signal for S-nitrosothiols may be confirmed by mixing the S-nitrosothiol compound with a slight molar excess (to the molar concentration of any S—NO bonds as well as to any site capable of binding $Hg^{+2}$) of Mercuric Chloride ($HgCl_2$). Additionally, a standard curve should be prepared using aliquots of the synthetic SNO-protein of interest diluted in the metalloprotein of interest: in this case, SNO-Hb, diluted in Hb.

6. Inject each unknown sample of ex-vivo Hb in triplicate. There is no-need to pre-treat the Hb with anything. It is important not to dilute the Hb to a concentration<200 μM before assay if tetrameric allosteric regulation is to be preserved. The pH, PO2 and PCO2, as well as concentrations of other allosteric regulators, should be preserved in the isolated Hb to be measured if the effect of $O_2$ and other parameters on Hb-SNO content is to be interpreted. The less manipulation between the time the blood is drawn and the time the time the Hb is assayed, the better. Note that metal chelators cannot be used as an anticoagulant in Hb isolation because they will chelate the Cu (I) in the assay.

7. The SNO-Hb concentration is derived from the evolved NO signal using the SNO-Hb in Hb and/or GSNO in Hb standard curve.

8. As a control, combine an aliquot of each unknown sample and a solution of mercuric chloride and repeat the injection to be certain that the signal is completely eliminated by the mercury solution.

a. Mercury solution for removing SNO—The mercury concentration needs to be 6-8× the concentration of Hb tetramer. Determine the concentration of the SNO-Hb solution by the Drabkin method or in a blood gas machine. Prepare a fresh solution of 0.125M $HgCl_2$ (67.9 mg Sigma #M1136, stored at room temperature in light tight box) up to 2 ml with distilled $H_2O$. Let stand 10 minutes at room temperature.

b. Inject into NOA—(Cu/cys assay using the NOA releases NO off the cys93 residue of Hb but not NO off the iron in the heme. Pretreatment of SNO protein with mercury breaks SNO bonds ONLY, hence, will remove the NO from cys93 but not from the iron. As a result, SNO protein pretreated with Hg gives no Cu/cys NO signal; the difference in chemiluminescence signal from the two unknown samples +/− Hg directly proportional to the # SNO bonds. Residual signal after treatment from Hg is due to HbFeNO).

Results—

Using the CO-saturated Copper-Cysteine ("3C") assay system, S-nitrosothiols ("SNOs") were selectively converted to NO in a CuCl saturated, 1 mM cysteine (pH 6.6) solution; NO was then detected by chemiluminescence (NOA 280i, Sievers, Boulder, Colo.) (see FIGS. 1 and 2).

In this assay, the cysteine has two functions. First, it forms CSNO by transnitrosation from other S-nitrosothiols: the $NO^+$ equivalent is reduced by Cu (I), forming NO (and Cu [II]). The transnitrosation equilibrium favors CSNO because of the 1) excess of reactant cysteine and 2) rapid loss of product CSNO. Second, the cysteine reduces product Cu (II), regenerating Cu (I). To permit assay of SNO bonds in the presence of vast excess of heme groups (FIG. 2), carbon monoxide (CO) was added to the inert gas flow through the reflux chamber to prevent NO autocapture by heme Fe(II), which could limit sensitivity. For this hemoglobin assay as described in the results, an important element is that the molecule was not pre-treated before it was assayed: the precise amount of S—NO present under the redox conditions present immediately before injection was measured.

Pre-treatment with cyanide, thiols, phosphate, high pH, low pH and a variety of other conditions will dramatically affect the affinity of hemoglobin, both for oxygen and for NO; therefore, interpretation of results made using such pretreatments will, of necessity, be flawed at best.

The 3C assay of the invention avoids this issue by preserving the molecule's structure until the moment of assay. The same is true for other metalloproteins, such as cytochrome c.

Example 2

SNO-Proteins in Erythrocytes (RBC's)

Here, the Cu/cysteine/CO assay was used in precisely the method described in Example 1. However, instead of isolating Hb from erythrocytes, intact erythrocytes were injected into the assay chamber after washing in physiological buffer at the precise pH and pCO2 at which the circulating erythrocytes had been drawn from the artery, vein, or capillary (See Table 1 and FIG. 3). Specific data ranges for red blood cell S-nitrosothiol content ($SNO_{RBC}$) are provided in Table 1. All other standards and controls apply.

This assay requires even less pre-assay manipulation than the SNO-Hb assay, and therefore provides an even more accurate picture of SNO-RBC content under specific conditions relevant in vivo. A potential disadvantage is that it measures all other erythrocytic SNO's, such as S-nitrosoanion exchange protein 1 and GSNO itself in RBC's, and therefore is not specific for SNO-Hb. However, this information (total RBC SNO content) may be of critical clinical relevance in a variety of conditions, such as pulmonary hypertension and sickle cell anemia. It may also be important in clinical monitoring of nitrovasodilator therapy, both systemic (i.e., nitroprusside or nitroglycerine) or inhaled (i.e., NO itself or ethyl nitrite).

TABLE 1

Human $SNO_{RBC}$ values

| Condition | $SNO_{RBC}$/Hb | Whole-blood $(SNO_{RBC})$* | Hb $SO_2$, % |
|---|---|---|---|
| Sepsis | $4.8 \times 10^{-4}$ to $2.5 \times 10^{-3}$ (median, $1.3 \times 10^{-3}$) | 1.2-6.25 μM (median, 3.25 μM) | 60 |
| Artery | $1.0 \times 10^{-4}$ to $2.2 \times 10^{-4}$ | 250-560 nM | 98 |
| Vein | $1.9 \times 10^{-5}$ to $1.3 \times 10^{-4}$ | 45-325 nM | 68 |
| Hypoxia (nadir) | $1.08 \times 10^{-5}$ | 27.5 nM | 34 |

*Estimated for 2.5 mM [Hb].

In sum, this method comprises the simultaneous reaction of the SNO bond with cysteine, (resulting in transnitrosation to form CSNO), CuCl (which catalyzes the conversion of CSNO to oxidized cysteine and NO gas) and carbon monoxide (CO) (which avidly binds to heme-Fe(II), preventing loss of NO to HbFe(II)NO or to nitrate via reaction of NO gas with oxyHb) in a solution of hypotonic water, which rapidly lyses RBCs and dilutes Hb to the point where they become dimers and lose allosteric regulation.

Specifically, the system involves a reflux cell connected to a sensitive NO chemiluminescence analyzer by Teflon tubing. The reflux (purge) chamber is filled to ⅓ volume with 3C solution with the addition of standard antifoam. The solution is gently bubbled with Grade 5 He, blended with CO scrubbed of metal carbonyls. The system must vent to a gas hood and the workstation must be equipped with a monitor-alarm to detect a CO gas leak. The water jacket around the reflux cell should be heated to 50° C.

Figure 2:
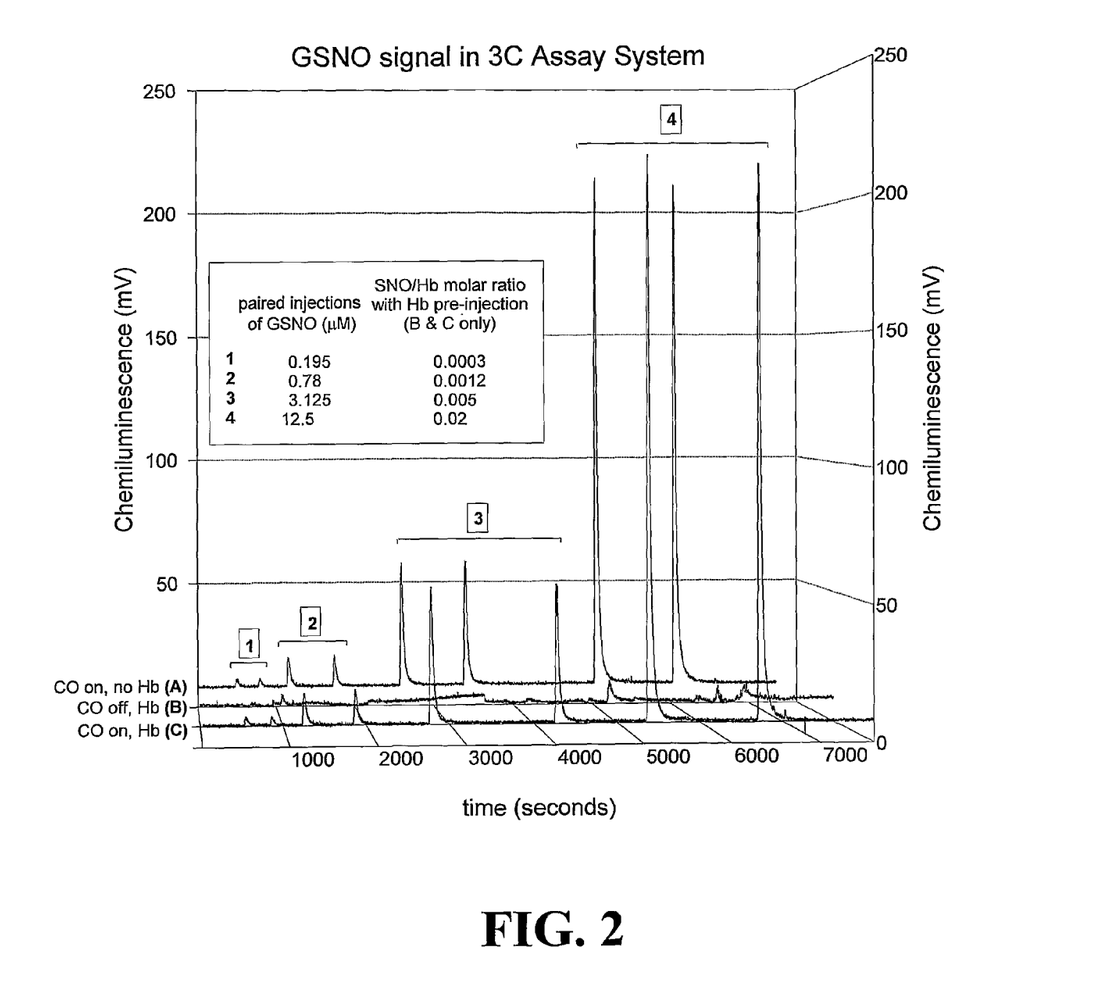
FIG. 2 graphically depicts the results of measuring the S-nitrosoglutathione (GSNO, a subset of the general class, S-nitrosothiol) signal in the 3C assay system of the invention. The ordinate represents chemiluminescence (mV) and the abscissa represents time in seconds. The chemiluminescence signal was measured in a 3C assay for: A) paired 20 μL injections, as indicated, of a GSNO dilution series (without CO); and B) the same injections of GSNO as for series A following pre-injection of 100 μL of 125 μM NO-depleted Hb into the reflux chamber. The mixture of Hb and GSNO in the reflux chamber simulates the SNO/Hb ratios noted; the signal for GSNO is lost, presumably to capture of NO by Heme Fe. In C) the signal for GSNO as in series (A) returns after adding carbonyl-purged CO to the inert gas stream, resolving the signal attenuation noted in (B). The ordinate represents chemiluminescence in mV and the abscissa represents time in seconds.

A standard curve should be generated using an S-nitrosothiol such as S-nitrosoglutathione with the pre-injection of SNO-depleted free Hb to mock the injection volume, [Hb] and to bracket the anticipated range of SNO/Hb molar ratios of the sample unknowns (FIG. 2).

The invention should not be construed to be limited solely to the assays and methods described herein, but should be construed to include other methods and assays as well. One of skill in the art will know that other assays and methods are available to perform the procedures described herein.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

Headings are included herein for reference and to aid in locating certain sections. These headings are not intended to limit the scope of the concepts described therein under, and these concepts may have applicability in other sections throughout the entire specification.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. The appended claims are intended to be construed to include all such embodiments and equivalent variations. Accordingly, the present invention is not intended to be limited to the embodiments shown herein but is to be accorded the widest scope consistent with the principles and novel features disclosed herein.

What is claimed is:

1. A method of measuring an S-nitrosothiol in an S-nitrosothiol-containing sample comprising the steps of:
    obtaining a test sample;
    reacting said test sample with cysteine and a non-iron transition metal under anaerobic conditions in a purge vessel;
    providing at least one chemical species which prevents binding of NO to iron containing substances; and
    analyzing said purge vessel output for NO generated from S-nitrosothiol, wherein the level of said NO is compared with the level of NO generated from an otherwise identical control sample or with the level of NO from a standard sample, thereby measuring S-nitrosothiol in a test sample.

2. The method of claim 1, wherein said reaction occurs at a temperature of about 40° C. to about 80° C. and a pH above about 5.0.

3. The method of claim 2, wherein said reaction occurs at a temperature of about 45° C. to about 60° C. and a pH of about 6.0 to about 7.0.

4. The method of claim 1, wherein the concentration of said non-iron transition metal is from about 0.1 µM to about to 10.0 µM.

5. The method of claim 1, wherein said transition metal is Cu(I).

6. The method of claim 5, wherein said Cu(I) is selected from the group consisting of CuCl, CuI, or CuBr.

7. The method of claim 1, wherein said cysteine concentration is from about 0.1 mM to about 10 mM.

8. The method of claim 1, wherein said purge vessel is purged with at least one gas.

9. The method of claim 8, wherein said at least one gas comprises an inert gas.

10. The method of claim 9, wherein said inert gas is helium.

11. The method of claim 9, further comprising a carbon monoxide gas free of metal carbonyls.

12. The method of claim 1, wherein said analysis for NO is a chemiluminescence analysis.

13. The method claim 1, wherein said sample is obtained from a subject selected from the group consisting of animals, mammals, humans, tissue culture, and cell culture.

14. The method of claim 13, wherein said sample is selected from the group of consisting of blood, sweat, tears, urine, feces, plasma, amniotic fluid, airway lining fluid/bronchoalveolar lavages, cerebrospinal fluid, joint fluid, pleural fluid, peritoneal fluid, cervical fluid, semen, tissue, cells, and derivatives, fractions, extracts, and isolates thereof.

15. The method of claim 14, wherein said sample, or derivative, fraction, extract or isolate thereof comprises proteins.

16. The method of claim 15, wherein said protein is an S-nitrosothiol protein.

17. The method of claim 16, wherein said S-nitrosothiol protein is a heme-containing protein.

18. The method of claim 17, wherein said heme-containing protein is hemoglobin.

19. The method of claim 14, wherein said sample is blood, further wherein an aliquot of said sample is also subjected to at least one additional assay which measures properties of blood relevant to hemoglobin allostery.

20. The method of claim 19, wherein said at least one additional assay measures partial oxygen pressure or partial carbon dioxide pressure.

21. The method of claim 14, wherein said cell is a red blood cell.

22. The method of claim 13, wherein said subject is a human.

* * * * *